(12) United States Patent
Isawa et al.

(10) Patent No.: US 8,709,516 B2
(45) Date of Patent: Apr. 29, 2014

(54) METHOD FOR CULTURING LACTIC ACID BACTERIUM AND METHOD FOR PRODUCING FERMENTED MILK

(75) Inventors: Kakuhei Isawa, Odawara (JP); Masayuki Kamijo, Odawara (JP)

(73) Assignee: Meiji Co., Ltd., Tokyo (JP)

( * ) Notice: Subject to any disclaimer, the term of this patent is extended or adjusted under 35 U.S.C. 154(b) by 19 days.

(21) Appl. No.: 13/260,254

(22) PCT Filed: Mar. 26, 2010

(86) PCT No.: PCT/JP2010/055438
§ 371 (c)(1),
(2), (4) Date: Sep. 23, 2011

(87) PCT Pub. No.: WO2010/113815
PCT Pub. Date: Oct. 7, 2010

(65) Prior Publication Data
US 2012/0027888 A1    Feb. 2, 2012

(30) Foreign Application Priority Data

Mar. 30, 2009   (JP) ................................. 2009-082073

(51) Int. Cl.
*A23C 9/12*    (2006.01)
(52) U.S. Cl.
USPC ........................................ 426/41; 435/253.6
(58) Field of Classification Search
USPC ........................................ 426/41; 435/253.6
See application file for complete search history.

(56) References Cited

U.S. PATENT DOCUMENTS

| | | | |
|---|---|---|---|
| 5,445,835 A * | 8/1995 | Vedamuthu | 426/9 |
| 5,527,505 A * | 6/1996 | Yamauchi et al. | 420/42 |
| 5,639,659 A * | 6/1997 | Barefoot et al. | 435/252.1 |
| 6,010,725 A | 1/2000 | Meister et al. | |
| 2011/0129568 A1 | 6/2011 | Fukui et al. | |

FOREIGN PATENT DOCUMENTS

| | | | |
|---|---|---|---|
| CN | 1507878 | | 6/2004 |
| CN | 1507879 | | 6/2004 |
| EP | 0 443 543 A2 | | 8/1991 |
| EP | 0 505 164 A2 | | 9/1992 |
| EP | 0 574 681 | | 12/1993 |
| JP | 4-211360 A | | 8/1992 |
| JP | 4-287636 A | | 10/1992 |
| JP | 8-187071 A | | 7/1996 |
| JP | 8-187072 A | | 7/1996 |
| JP | 10-057031 A | | 3/1998 |
| JP | 2003-235529 A | | 8/2003 |
| JP | 2004-283109 A | | 10/2004 |
| JP | 2008-005834 A | | 1/2008 |
| WO | WO 03/045987 | | 6/2003 |
| WO | WO03045987 | * | 6/2003 ........... C07K 14/315 |
| WO | WO-2007-138993 A1 | | 12/2007 |
| WO | WO 2008/016214 | | 2/2008 |
| WO | WO-2010-001580 A1 | | 1/2010 |

OTHER PUBLICATIONS

Zhu, W. M. et al. 2000. Isolation and characterization of a new bacteriocin form Lactobacillus gasseri KT7. J. Appl. Microbiol. 88: 877-886.*
Takeo Kato et al., "Growth of Nisin-Producing Lactococci in Cooked Rice Supplemented with Soybean Extract and its Application to Inhibition of *Bacillus subtilis* in Rice Miso", Biosci. Biotechnol. Biochem., 65(2), Feb. 2001, pp. 330-337.
Linda J. Harris et al., "Novel Paired Starter Culture System for Sauerkraut, Consisting of a Nisin-Resistant Leuconostoc mesenteroides Strain and a Nisin-Produsing *Lactococcus lactis* Strain", Applied and Environmental Microbiology, vol. 58, No. 5, May 1992, pp. 1484-1489.
Liu X, et al., "Continuous nisin production in laboratory media and whey permeate by immobilized *Lactococcus lactis*" Process Biochemistry, Elsevier, NL, vol. 40, No. 1, Jan. 1, 2005, pp. 13-24.
Bertrand N. et al., "High nisin-Z production during repeated-cycle batch cultures in supplemented whey permeate using immobilized *Lactococcus lactis* UL719" International Dairy Journal, Elsevier Applied Science, Barking, GB, vol. 11, Jan. 1, 2001, pp. 953-960.

* cited by examiner

*Primary Examiner* — D. Lawrence Tarazano
*Assistant Examiner* — Hamid R Badr
(74) *Attorney, Agent, or Firm* — Rabin & Berdo, P.C.

(57) ABSTRACT

A method for culturing lactic acid bacteria includes (a) adding a proteolytic enzyme to an aqueous whey solution containing whey and water to thereby prepare a culture solution containing whey degraded by the proteolytic enzyme; (b) inoculating the culture solution with *Lactobacillus gasseri* which is a bacteriocin-producing lactic acid bacteria; and (c) maintaining the culture solution inoculated with the bacteriocin-producing lactic acid bacteria at a pH of not lower than 5.2 and not higher than 5.8 to provide cultured lactic acid bacteria. After the completion of culturing, the culture solution is centrifuged to separate a concentrated cell suspension containing the lactic acid bacterium in a concentrated form. The concentrated cell suspension has extremely high antibacterial activity, several tens of thousands AU, and is usable as a food preservative. Yogurt is produced by fermenting a yogurt mix to which 0.01% to 0.1% by weight of the concentrated cell suspension is added.

8 Claims, 6 Drawing Sheets

Fig. 1

COMPOSITION OF WHEY DEGRADATION MEDIUM (EXAMPLE 1)

| RAW MATERIAL | BLEND RATIO [WT%] |
|---|---|
| WHEY POWDER | 8.70 |
| WHEY PROTEIN CONCENTRATE (WPC80) | 1.50 |
| PROTEASE A "AMANO" G | 0.10 |
| BREWER'S YEAST EXTRACT (MEAST) | 0.20 |
| FISH EXTRACT (TUNA, OCEANIC BONITO) | 0.50 |
| SODIUM ASCORBATE Na | 0.10 |
| FERROUS SULFATE | 0.05 |
| EMULSIFIER (SUN SOFT Q-17S) | 0.05 |
| WATER | 88.80 |

Fig. 2

RESULT OF CULTURE OF LACTOBACILLUS GASSERI OLL2959

| | VIABLE CELL COUNT (cfu/ml) | ANTIBACTERIAL ACTIVITY (AU/ml) | ANTIBACTERIAL ACTIVITY (AU/1×10$^9$cfu) |
|---|---|---|---|
| EXAMPLE 1 (NEUTRAL CULTURE) | $1.81 \times 10^{10}$ | 72400 | 4000 |
| COMPARATIVE EXAMPLE 1 (STATIC CULTURE) | $2.63 \times 10^9$ | LOWER THAN 100 | LOWER THAN 40 |

Fig. 3

COMPOSITION OF WHEY DEGRADATION MEDIUM (EXAMPLE 2)

| RAW MATERIAL | BLEND RATIO [WT%] |
|---|---|
| WHEY POWDER | 8.70 |
| WHEY PROTEIN CONCENTRATE (WPC80) | 1.50 |
| PROTEASE A "AMANO" G | 0.10 |
| BREWER'S YEAST EXTRACT (MEAST) | 0.20 |
| FISH EXTRACT (TUNA, OCEANIC BONITO) | 0.50 |
| SODIUM ASCORBATE Na | 0.10 |
| FERROUS SULFATE | 0.05 |
| EMULSIFIER (SUN SOFT 81S) | 0.05 |
| WATER | 88.80 |

Fig. 4

RESULT OF CULTURE OF LACTOBACILLUS GASSERI OLL2959

| | VIABLE CELL COUNT (cfu/ml) | ANTIBACTERIAL ACTIVITY (AU/ml) | ANTIBACTERIAL ACTIVITY (AU/$1 \times 10^9$cfu) |
|---|---|---|---|
| EXAMPLE 2 (NEUTRAL CULTURE) | $1.84 \times 10^{10}$ | 51200 | 2800 |
| COMPARATIVE EXAMPLE 2 (STATIC CULTURE) | $2.63 \times 10^9$ | LOWER THAN 100 | LOWER THAN 40 |

COMPOSITION OF YOGURT MIX (EXAMPLE 4)

| RAW MATERIAL | BLEND RATIO [WT%] | | |
|---|---|---|---|
| | BLEND A | BLEND B | BLEND C |
| MILK (RAW MILK) | 83.90 | 83.90 | 83.90 |
| SKIMMED MILK POWDER | 1.51 | 1.51 | 1.51 |
| WHEY PROTEIN CONCENTRATE (WPC34) | 0.80 | 0.80 | 0.80 |
| STARTER (MEIJI BULGARIA YOGURT) | 2.00 | 2.00 | 2.00 |
| CONCENTRATED CELL SUSPENSION (OLL2959) | 0.00 | 0.05 | 0.10 |
| WATER | 11.79 | 11.74 | 11.69 |

CHANGE IN ACIDITY OF YOGURT OVER TIME IN EXAMPLE 4

CHANGE IN ACIDITY OF YOGURT OVER TIME IN EXAMPLE 4

COMPOSITION OF YOGURT MIX (EXAMPLE 5)

| RAW MATERIAL | BLEND RATIO [WT%] | |
|---|---|---|
| | BLEND D | BLEND E |
| MILK (RAW MILK) | 84.20 | 84.20 |
| SKIMMED MILK POWDER | 1.76 | 1.76 |
| WHEY PROTEIN ISOLATE (WPI) | 0.20 | 0.20 |
| SUGAR | 4.50 | 4.50 |
| STARTER (MEIJI TOKACHI YOGURT) | 3.00 | 3.00 |
| CONCENTRATED CELL SUSPENSION (OLL2959) | 0.00 | 0.05 |
| WATER | 6.34 | 6.29 |

CHANGE IN ACIDITY OF YOGURT OVER TIME IN EXAMPLE 5

METHOD FOR CULTURING LACTIC ACID BACTERIUM AND METHOD FOR PRODUCING FERMENTED MILK

TECHNICAL FIELD

The present invention relates to a method for culturing bacteriocin-producing lactic acid bacterium and a method for producing fermented milk containing the bacteriocin-producing lactic acid bacterium.

BACKGROUND ART

Fermented milk such as yogurt is produced by adding a starter to raw material milk (yogurt mix) into which raw milk, skimmed milk powder, whey protein, or the like are mixed and fermenting the yogurt mix. As the starter, used is lactic acid bacterium such as *Lactobacillus bulgaricus*, *Streptococcus thermophilus*, or the like.

After the production, the yogurt mix is cooled to a temperature of 0 to 10 degrees and shipped in cold storage. Since the lactic acid bacterium is alive in the yogurt in cold storage, the yogurt is gradually fermented in the course of distribution and during the period of storage at home or the like and the acidity thereof increases. As a result, the flavor of the yogurt is changed even within the freshness date.

It is well known that some kinds of lactic acid bacterium produces an antibacterial protein or peptide called a bacteriocin, As shown in the following Patent Documents 1 to 3, it is possible to improve the preservative quality of foods by using the bacteriocin-producing lactic acid bacterium.

In the invention of Patent Document 1, bacteriocin-producing *Lactococcus lactis* is used as a starter for yogurt. *Lactococcus lactis* produces a bacteriocin as the yogurt mix is fermented. Since the bacteriocin produced by *Lactococcus lactis* suppresses an increase in the acidity of yogurt, it is possible to improve the preservative quality of yogurt.

In the invention of Patent Document 2, *Bifidobacterium* and *Lactococcus lactis* are cocultured by using a liquid culture medium of which the main ingredients are milk and milk constituents. By adding the culture solution after the coculture to foods (bread, Udon noodles (Japanese noodles), or the like) as a food preservative, it is possible to improve the preservative quality of the foods and give good flavor to the foods.

Patent Document 3 shows a flavor improving agent obtained by culturing *Lactococcus lactis* with a whey medium to which yeast extract or the like is added and removing the *Lactococcus lactis* from the whey medium after the culture. By using this flavor improving agent, it is possible to get rid of the fishiness of the fish (the fishy odor) and give good flavor (taste) to foods.

[Patent Document 1] Japanese Patent Application Laid Open Gazette No. 4-211360
[Patent Document 2] Japanese Patent Application Laid Open Gazette No. 8-187071
[Patent Document 3] Japanese Patent Application Laid Open Gazette No. 2004-283109

As discussed above, the invention of Patent Document 1 uses the bacteriocin-producing *Lactococcus lactis* as a starter. For this reason, it is difficult to suppress an increase in the acidity of the yogurt for which *Lactococcus lactis* is not used as a starter.

For the purpose of suppressing an increase in the acidity of the yogurt in the course of distribution and during the period of storage, the food preservative used in Patent Document 2 or the flavor improving agent used in Patent Document 3 may be added the yogurt mix as an additive. In a case where the additive is added to the yogurt mix at a certain rate, however, there is a possibility that the yeast extract which is a material of the additive may damage the original flavor of the yogurt. Therefore, in the case where the culture of the bacteriocin-producing lactic acid bacterium is added to the yogurt mix, it is desirable that the amount of culture to be added should be made as small as possible.

DISCLOSURE OF INVENTION

The present invention is intended for a method for culturing lactic acid bacterium. According to the present invention, the method for culturing lactic acid bacterium comprises a culture solution preparation step of preparing a culture solution containing whey degraded by a proteolytic enzyme and a culture step of inoculating bacteriocin-producing lactic acid bacterium into the culture solution and culturing the lactic acid bacterium while maintaining the culture solution inoculated with the lactic acid bacterium at pH of not lower than 5 and not higher than 6.

By the method for culturing lactic acid bacterium according to the present invention, it is possible to obtain a culture solution having antibacterial activity which is about several tens times as high as the culture solution obtained by the prior-art culturing method. In other words, by the method for culturing lactic acid bacterium of the present invention, it is possible to produce a bacteriocin with high efficiency.

The present invention is also intended for a method for producing fermented milk. According to the present invention, the method for producing fermented milk comprises a raw material milk producing step of producing a yogurt mix, a concentrated cell suspension producing step of culturing a bacteriocin producer which is bacteriocin-producing lactic acid bacterium to thereby produce a concentrated cell suspension containing the bacteriocin producer in a concentrated form, an addition step of adding not less than 0.01% and not more than 0.1% by weight of the concentrated cell suspension, based on the total weight of the yogurt mix, to the yogurt mix, and a fermentation step of fermenting the yogurt mix to which the concentrated cell suspension is added, and in the method of the present invention, the concentrated cell suspension producing step includes a culture solution preparation step of preparing a culture solution containing whey degraded by a proteolytic enzyme, a culture step of inoculating the bacteriocin producer into the culture solution and culturing the bacteriocin producer while maintaining the culture solution inoculated with the bacteriocin producer at pH of not lower than 5 and not higher than 6, and a separation step of separating the concentrated cell suspension from the culture solution inoculated with the bacteriocin producer.

By the method for producing fermented milk according to the present invention, the amount of concentrated cell suspension to be added to the yogurt mix as an additive can be reduced. It is therefore possible to prevent an increase in the acidity of yogurt without damaging the original flavor of the yogurt.

Therefore, it is an object of the present invention to provide a method for culturing lactic acid bacterium by which lactic acid bacterium can produce a bacteriocin with high efficiency and a method for producing fermented milk by which an increase in the acidity of fermented milk can be suppressed.

These and other objects, features, aspects and advantages of the present invention will become more apparent from the following detailed description of the present invention when taken in conjunction with the accompanying drawings.

BRIEF DESCRIPTION OF DRAWINGS

FIG. 1 is a view showing the composition of a whey degradation medium used in Example 1;

FIG. 2 is a view showing a result of the culture of *Lactobacillus gasseri* in Example 1;

FIG. 3 is a view showing the composition of a whey degradation medium used in Example 2;

FIG. 4 is a view showing a result of the culture of *Lactobacillus gasseri* in Example 2;

BEST MODE FOR CARRYING OUT THE INVENTION

Figures 5, 6:
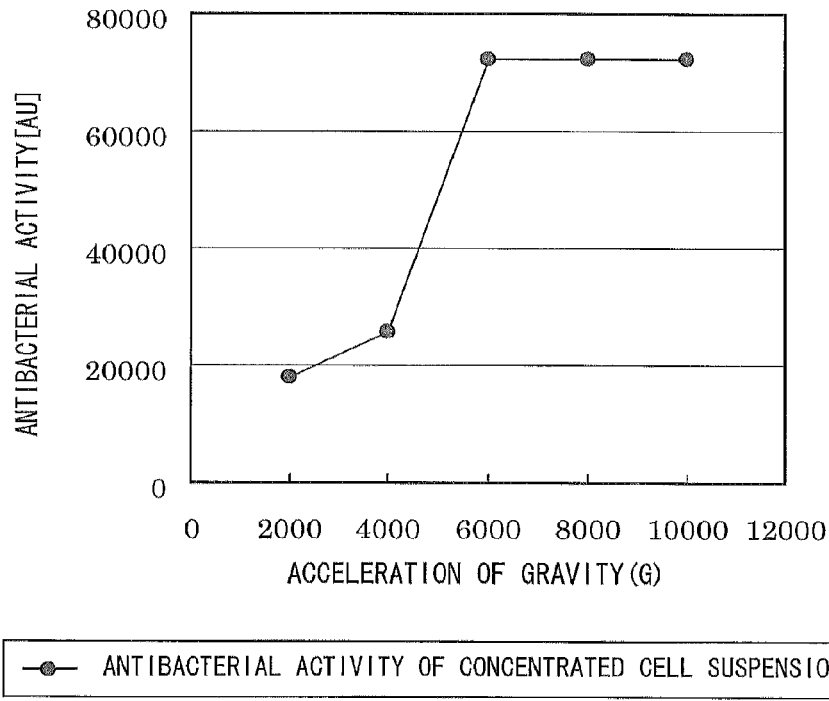
FIG. 5 is a graph showing a correspondence relation between the acceleration of gravity during centrifugal separation and the antibacterial activity of a concentrated cell suspension.
FIG. 6 is a view showing the respective compositions of yogurt mixes used in Example 4.

Hereinafter, the preferred embodiment of the present invention will be discussed. In a method for culturing lactic acid bacterium in accordance with the preferred embodiment, lactic acid bacterium is cultured while an alkaline solution is being added to a culture medium so that the pH of the culture medium can be maintained within a certain range (not lower than 5 and not higher than 6). It is thereby possible to obtain a culture of the lactic acid bacterium having very high antibacterial activity per viable cell count.

In a method for culturing lactic acid bacterium in accordance with this preferred embodiment, the lactic acid bacterium to be cultured is bacteriocin-producing lactic acid bacterium (hereinafter, referred to as "a bacteriocin producer"). The lactic acid bacterium which belongs to *Lactobacillus* such as *Lactobacillus gasseri*, the lactic acid bacterium which belongs to *Lactococcus* such as *Lactococcus lactis*, and the like can be cultured by using the method for culturing lactic acid bacterium in accordance with this preferred embodiment. Specifically, the lactic acid bacterium includes, for example, *Lactobacillus gasseri* OLL2959 (NITE BP-224, NITE Patent Microorganisms Depositary (NPMD)), *Lactococcus lactis* subsp. *lactis* OLS3311 (FERM BP-10966, International Patent Organism Depositary (IPOD)), *Lactococcus lactis* subsp. *cremoris* OLS3312 (FERM BP-10967, International Patent Organism Depositary (IPOD)), and the like.

Herein, specific discussion will be made on the method for culturing lactic acid bacterium in accordance with this preferred embodiment. First, a proteolytic enzyme such as a protease is added to an aqueous whey solution containing whey, to thereby degrade whey protein in the aqueous whey solution. Before adding the proteolytic enzyme, whey protein such as a Whey Protein Concentrate (WPC), a Whey Protein Isolate (WPI), or the like may be added to the aqueous whey solution.

Next, yeast extract such as brewer's yeast extract is added to the aqueous whey solution, to thereby prepare a whey degradation medium to be used for the culture of the bacteriocin producer. To the whey degradation medium, meat extract, fish extract, or the like besides the whey protein may be added as a nitrogen source. Further, to the whey degradation medium, an inorganic nutrient such as ferrous sulfate, magnesium sulfate, or the like, and an emulsifier such as deca glycerol monooleate, sorbitan monooleate, or the like may be added. Sodium ascorbate or the like may be also added to the whey degradation medium.

The bacteriocin producer is inoculated into the whey degradation medium, to thereby culture the bacteriocin producer. Preferably, the bacteriocin producer is cultured until the pH of the whey degradation medium becomes not higher than 6 and then the bacteriocin producer continues to be cultured while the pH of the whey degradation medium in which the bacteriocin producer is cultured is controlled to be in a range of not lower than 5 and not higher than 6. More preferably, the bacteriocin producer is cultured until the pH of the whey degradation medium becomes not higher than 5.8 and then the bacteriocin producer continues to be cultured while the pH of the whey degradation medium is controlled to be in a range of not lower than 5.2 and not higher than 5.8. Still more preferably, the bacteriocin producer continues to be cultured while the pH of the whey degradation medium is controlled to be in a range of not lower than 5.5 and not higher than 5.8. The pH can be controlled by adding an alkaline solution to the whey degradation medium. As the alkaline solution, an aqueous potassium carbonate solution, an aqueous sodium hydrogen carbonate solution, or the like may be used.

After culturing the bacteriocin producer, a concentrated cell suspension containing the bacteriocin producer in concentrated form is separated from the whey degradation medium (culture solution) in which the bacteriocin producer is cultured. The concentrated cell suspension can be separated by centrifugal separation or membrane separation. In the case of using centrifugal separation, it is preferable that the concentrated cell suspension should be separated at acceleration of gravity of not lower than 6000 (G).

The concentrated cell suspension of the bacteriocin producer which is thus obtained has high antibacterial activity which is several tens times or more as high as that of the concentrated cell suspension of the bacteriocin producer which is cultured without controlling the pH of the whey degradation medium during the culture. In other words, by culturing the bacteriocin producer while maintaining the whey degradation medium at pH ranging from 5 to 6, it is possible to obtain the concentrated cell suspension having high antibacterial activity with high efficiency while controlling the antibacterial activity of the concentrated cell suspension.

In a case where the concentrated cell suspension in accordance with this preferred embodiment is added to foods as a food preservative, the amount of concentrated cell suspension to be added to foods in accordance with the preferred embodiment can be made smaller than the amount of food preservatives which is conventionally needed. The concentrated cell suspension of this preferred embodiment, which is added to foods as a food preservative, can improve the preservative quality of foods while suppressing any change in the original flavor of the foods.

Next, specific discussion will be made on the method for producing fermented milk (yogurt) in accordance with this preferred embodiment. First, a yogurt mix which is raw material milk is prepared. The yogurt mix can be prepared by, for example, mixing skimmed milk powder, whey protein, water, and the like into raw milk. Further, sugar, fruit flesh, fruit juice, or the like may be added to the yogurt mix.

After homogenizing and disinfecting the yogurt mix in the same manner as conventionally done, the yogurt mix is inoculated with a starter, the bacteriocin producer obtained by the above-discussed method for culturing lactic acid bacterium, and the concentrated cell suspension thereof. Preferably, the amount of concentrated cell suspension of the bacteriocin producer to be inoculated is not less than 0.01 weight % (WT %) and not more than 0.1 WT %, based on the total weight of the yogurt mix. More preferably, the amount of concentrated cell suspension of the bacteriocin producer to be inoculated is not less than 0.01 WT % and not more than 0.05 WT %.

The lactic acid bacterium to be used as the starter may be the same lactic acid bacterium as the bacteriocin producer or different one. Further, the concentrated cell suspension may be added to the yogurt mix before the processes for homogenizing and disinfecting the yogurt mix.

The yogurt mix inoculated with the bacteriocin producer and the concentrated cell suspension thereof is fermented, to thereby produce yogurt. The fermentation conditions thereof may be the same as conventional conditions. In the yogurt produced by the method discussed in this preferred embodiment, an increase in the acidity from immediately after the production can be suppressed as compared with the yogurt to which no concentrated cell suspension is added. The reason therefor is that the high-concentration bacteriocin contained in the concentrated cell suspension suppresses the activity of the *Lactobacillus bulgaricus* in the yogurt. Thus, in the yogurt produced by the method discussed in this preferred embodiment, the good flavor that the yogurt has immediately after the production can be maintained over the freshness date thereof (for about two weeks) more steadily as compared with in conventional ones.

In the method for producing fermented milk of this preferred embodiment, it is possible to reduce the amount of concentrated cell suspension to be used as a food preservative to about one tenth of the amount of food preservative which is conventionally used. Therefore, it is possible to prevent the original flavor of the yogurt from being damaged by addition of the concentrated cell suspension.

EXAMPLES

Hereinafter, with reference to figures, discussion will be made on Examples of the method for culturing lactic acid bacterium in accordance with the present invention.

Example 1

FIG. 1 is a view showing the composition of a whey degradation medium used in Example 1. First, the whey degradation medium to be used in Example 1 is prepared. Specifically, an aqueous whey solution is prepared by mixing 8.70% by weight of whey powder (manufactured by Meiji Dairies Corporation), 1.50% by weight of Whey Protein Concentrate (WPC80, manufactured by New Zealand Milk Products Co., Ltd.), and 88.80% by weight of water, based on the total weight of the whey degradation medium. Then, whey protein in the aqueous whey solution is degraded by adding 0.10% by weight of the proteolytic enzyme (Protease A "Amano" G, manufactured by Amano Enzyme Inc.) to the aqueous whey solution.

After that, 0.20% by weight of brewer's yeast extract (manufactured by Asahi Breweries, Ltd.), 0.50% by weight of fish extract (manufactured by Maruha Nichiro Foods, Inc.), 0.10% by weight of sodium ascorbate, 0.05% by weight of ferrous sulfate ($FeSO_4$), and 0.05% by weight of an emulsifier (Sun Soft Q-17S (Deca Glycerol Monooleate) manufactured by Taiyo Kagaku Co., Ltd.) are added to the aqueous whey solution in which the whey protein is degraded, to thereby prepare the whey degradation medium.

Next, *Lactobacillus gasseri* OLL2959 (NITE BP-224, NITE Patent Microorganisms Depositary (NPMD)) is inoculated into the whey degradation medium so that the viable cell count will be 2 to $4 \times 10^7$ cfu/ml. After the *Lactobacillus gasseri* OLL2959 is cultured until the pH of the whey degradation medium becomes 5.5, the *Lactobacillus gasseri* OLL2959 is neutrally cultured. Specifically, the *Lactobacillus gasseri* OLL2959 is cultured (neutral culture) for 22 hours at a temperature of 34 degrees while an aqueous potassium carbonate solution (40 WT %) is added to the whey degradation medium, being stirred, so that the pH of the whey degradation medium will be always not lower than 5.5. The neutral culture is performed under the anaerobic condition where carbon dioxide is blown in the environment. After the neutral culture, the number of viable cells of the *Lactobacillus gasseri* OLL2959 in the whey degradation medium (culture solution) is measured by pour plate culture using a BCP medium. The viable cell count of the *Lactobacillus gasseri* OLL2959 is $1.81 \times 10^{10}$ cfu/ml.

By centrifuging the whey degradation medium (culture solution) after the neutral culture (at acceleration of gravity of 6000 G), obtained is a concentrated cell suspension of *Lactobacillus gasseri* OLL2959 in accordance with Example 1. The antibacterial activity of the concentrated cell suspension of Example 1 is measured by using such a method as discussed later. The measurement result is that the antibacterial activity of the concentrated cell suspension of Example 1 is 72400 AU (Arbitrary Unit) per 1 ml. Further, the antibacterial activity of the concentrated cell suspension of Example 1 is about 4000 AU per $1 \times 10^9$ cfu.

Further, the *Lactobacillus gasseri* OLL2959 is neutrally cultured by using the whey degradation medium of Example 1, with the condition of the pH of the whey degradation medium being changed. The result is that the antibacterial activity of the concentrated cell suspension obtained by the neutral culture under the condition that the pH ranges from 5.2 to 5.8 has the same value as that of the antibacterial activity of the concentrated cell suspension of Example 1. The antibacterial activity of the concentrated cell suspension obtained by the neutral culture under the condition that the pH ranges from 5 to 6 has a value slightly lower than that of the antibacterial activity of the concentrated cell suspension of Example 1.

In order to check the effect of the neutral culture, the whey degradation medium inoculated with the *Lactobacillus gasseri* OLL2959 in the same procedure as in Example 1 is left still for 20 hours at a temperature of 37 degrees to statically culture the *Lactobacillus gasseri* OLL2959 (Comparative Example 1). By centrifuging the statically cultured whey degradation medium (culture solution) (at acceleration of gravity of 6000 G), obtained is a concentrated cell suspension in accordance with Comparative Example 1.

In the whey degradation medium (culture solution) after the static culture, the viable bacterial count of the *Lactobacillus gasseri* OLL2959 is $2.63 \times 10^9$ cfu/ml. The antibacterial activity of the concentrated cell suspension of Comparative Example 1 is lower than 100 AU per 1 ml of the concentrated cell suspension. The antibacterial activity of the concentrated cell suspension of Comparative Example 1 is lower than about 40 AU per $1\times10^9$ cfu.

FIG. 2 shows the respective measurement results on the viable cell count of the cultured *Lactobacillus gasseri* OLL2959 and the antibacterial activity of the concentrated cell suspension in Example 1 and Comparative Example 1. As discussed above, the antibacterial activity of the concentrated cell suspension of Example 1 is 4000 AU per $1\times10^9$ cfu while the antibacterial activity of the concentrated cell suspension of Comparative Example 1 is lower than about 40 AU per $1\times10^9$ cfu. In other words, the antibacterial activity per viable cell count of the concentrated cell suspension (Example 1) obtained by the neutral culture is about 100 times as much as the antibacterial activity per viable cell count of the concentrated cell suspension (Comparative Example 1) obtained by the static culture.

Further, the viable cell count of the *Lactobacillus gasseri* OLL2959 in the whey degradation medium (culture solution) after the neutral culture is larger than the viable cell count in the whey degradation medium (culture solution) after the static culture by about one order of magnitude. It can be understood from the above that a bacteriocin is produced with high efficiency since the *Lactobacillus gasseri* OLL2959 is made active by maintaining the whey degradation medium at a pH of not lower than 5.5 during the neutral culture.

Thus, by performing the neutral culture of the bacteriocin producer while controlling the pH of the whey degradation medium to range from 5 to 6 during the culture, it is possible to control the antibacterial activity of the concentrated cell suspension to be at very high level.

Example 2

FIG. 3 is a view showing the composition of a whey degradation medium used in Example 2. In order to prepare the whey degradation medium to be used in Example 2, the aqueous whey solution in which the whey protein is degraded is prepared in the same procedure as in Example 1.

Then, 0.20% by weight of brewer's yeast extract (manufactured by Asahi Breweries, Ltd.), 0.50% by weight of fish extract (manufactured by Maruha Nichiro Foods, Inc.), 0.10% by weight of sodium ascorbate, 0.05% by weight of ferrous sulfate ($FeSO_4$), and 0.05% by weight of an emulsifier (Sun Soft 81S (Sorbitan Monooleate) manufactured by Taiyo Kagaku Co., Ltd.) are added to the aqueous whey solution in which the whey protein is degraded, to thereby prepare the whey degradation medium. The emulsifier used in Example 2 is different from that used in Example 1.

Next, *Lactobacillus gasseri* OLL2959 is inoculated into the whey degradation medium so that the viable cell count will be 2 to $4\times10^7$ cfu/ml. Like in Example 1, after the *Lactobacillus gasseri* OLL2959 is cultured until the pH of the whey degradation medium becomes 5.5, the *Lactobacillus gasseri* OLL2959 is neutrally cultured. Specifically, the *Lactobacillus gasseri* OLL2959 is neutrally cultured for 22 hours at a temperature of 34 degrees while an aqueous potassium carbonate solution (40 WT %) is added to the whey degradation medium so that the pH of the whey degradation medium will be always not lower than 5.5. After the neutral culture, the number of viable cells of the *Lactobacillus gasseri* OLL2959 in the whey degradation medium (culture solution) is measured by the same method as in Example 1. The viable cell count of the *Lactobacillus gasseri* OLL2959 is $1.84\times10^{10}$ cfu/ml.

By centrifuging the whey degradation medium (culture solution) after the neutral culture (at acceleration of gravity of 6000 G), separated is a concentrated cell suspension in accordance with Example 2. The antibacterial activity of the concentrated cell suspension of Example 2 is 51200 AU per 1 ml. The antibacterial activity of the concentrated cell suspension of Example 2 is about 2800 AU per $1\times10^9$ cfu. The measurement of the antibacterial activity is performed by the same method as in Example 1 (discussed later).

Further, the *Lactobacillus gasseri* OLL2959 is neutrally cultured by using the whey degradation medium of Example 2, with the condition of the pH of the whey degradation medium being changed. The result is that the antibacterial activity of the concentrated cell suspension obtained by the neutral culture under the condition that the pH ranges from 5.2 to 5.8 has the same value as that of the antibacterial activity of the concentrated cell suspension of Example 2. The antibacterial activity of the concentrated cell suspension obtained by the neutral culture under the condition that the pH ranges from 5 to 6 has a value slightly lower than that of the antibacterial activity of the concentrated cell suspension of Example 2.

In order to check the effect of the neutral culture, the whey degradation medium inoculated with the *Lactobacillus gasseri* OLL2959 in the same procedure as in Example 2 is left still for 20 hours at a temperature of 37 degrees to perform static culture (Comparative Example 2). By centrifuging the statically cultured whey degradation medium (culture solution) (at acceleration of gravity of 6000 G), a concentrated cell suspension in accordance with Comparative Example 2 is separated.

In the whey degradation medium (culture solution) after the static culture, the viable cell count of the *Lactobacillus gasseri* OLL2959 is $2.63\times10^9$ cfu/ml. The antibacterial activity of the concentrated cell suspension of Comparative Example 2 is lower than 100 AU per 1 ml of the concentrated cell suspension. The antibacterial activity of the concentrated cell suspension of Comparative Example 2 is lower than about 40 AU per $1\times10^9$ cfu.

FIG. 4 shows the respective measurement results on the viable cell count of the cultured *Lactobacillus gasseri* OLL2959 and the antibacterial activity of the concentrated cell suspension in Example 2 and Comparative Example 2. As discussed above, the antibacterial activity of the concentrated cell suspension of Example 2 is 2800 AU per $1\times10^9$ cfu while the antibacterial activity of the concentrated cell suspension of Comparative Example 2 is lower than about 40 AU per $1\times10^9$ cfu. In other words, the antibacterial activity per viable cell count of the concentrated cell suspension (Example 2) obtained by the neutral culture is 70 or more times as much as the antibacterial activity per viable cell count of the concentrated cell suspension (Comparative Example 2) obtained by the static culture.

Further, the viable cell count of the *Lactobacillus gasseri* OLL2959 after the neutral culture is larger than the viable cell count of the *Lactobacillus gasseri* OLL2959 after the static culture by about one order of magnitude. Also in Example 2, it can be understood that a bacteriocin is produced with high efficiency since the *Lactobacillus gasseri* OLL2959 is made active.

Thus, by performing the neutral culture of the *Lactobacillus gasseri* OLL2959 under the condition of Example 2, it is possible to control the antibacterial activity of the concentrated cell suspension to be at very high level. Further, since the antibacterial activities of the concentrated cell suspensions in Examples 1 and 2 are several tens to several hundreds times as much as the antibacterial activities of the concentrated cell suspensions in Comparative Examples 1 and 2, respectively, it can be seen that the emulsifier which can be used in the whey degradation medium is not particularly limited to anything.

(Method for Measuring Antibacterial Activity)

Next, discussion will be made on a method for measuring the antibacterial activity of the concentrated cell suspension of the *Lactobacillus gasseri* OLL2959, taking the concentrated cell suspension of Example 1 as an example. The antibacterial activities of the concentrated cell suspensions of Example 2 and Comparative Examples 1 and 2 are also measured by the same method.

An MRS medium (manufactured by Becton, Dickinson and Company) currently on the market is used. A test medium is prepared by adding 0.1% volume/volume (v/v) of indicator bacteria, based on the MRS medium. As the indicator bacterium, used is *Lactobacillus delbrueckii* subsp. *bulgaricus* ATCC11842 (type strain).

The frozen and stored concentrated cell suspension of Example 1 is kept in a hot water bath for 5 minutes, and then a 1% (v/v) aqueous solution of the concentrated cell suspension of Example 1 is prepared. The aqueous solution of the concentrated cell suspension is progressively diluted by 2-fold and a plurality of diluted solutions of the concentrated cell suspension which are different in the level of dilution rate are obtained. The levels of dilution rate ranges from 8 to 12. The $2^8$-fold to $2^{12}$-fold diluted solutions of the concentrated cell suspension are thereby prepared. These diluted solutions are added to the test media, respectively, and then the test media to which the $2^8$-fold to $2^{12}$-fold diluted solutions are added are anaerobically cultured by using AnaeroPack-Anaero (manufactured by Mitsubishi Gas Chemical Company, Inc.) for 24 hours at a temperature of 37 degrees.

After the anaerobic culture, checked is the maximum level (n) of dilution rate at which no indicator bacterium is grown. Then, on the basis of the maximum level (n) of dilution rate and the concentration (0.01:1%) of the aqueous solution of the concentrated cell suspension, the antibacterial activity (AU) of the concentrated cell suspension of Example 1 is obtained. The antibacterial activity can be obtained on the basis of the following formula.

Antibacterial activity (AU)=the maximum level ($n$) of dilution rate/the concentration (0.01) of the aqueous solution of the concentrated cell suspension

Example 3

In Example 3, an examination is made on conditions for centrifugal separation of the concentrated cell suspension of *Lactobacillus gasseri* which is neutrally cultured. By setting various values for acceleration of gravity, the whey degradation medium (culture solution) after the neutral culture in Example 1 is centrifuged. Then, the respective antibacterial activities of the concentrated cell suspensions are obtained under different conditions for centrifugal separation.

FIG. 5 is a graph showing a relation between the acceleration of gravity and the antibacterial activity of the concentrated cell suspension. As shown in FIG. 5, as the acceleration of gravity during the centrifugal separation increases, the antibacterial activity of the concentrated cell suspension is increased. Then, at the acceleration of gravity of not lower than 6000 G during the centrifugal separation, the antibacterial activity becomes constant (about 72400 AU). From this result, it can be clearly seen that it is possible to obtain a concentrated cell suspension having high antibacterial activity with high efficiency by centrifugal separation of the concentrated cell suspension at the acceleration of gravity of not lower than 6000 G.

Hereafter, discussion will be made on methods for producing yogurt by using the concentrated cell suspension in accordance with Example 1, as Examples of the method for producing fermented milk in accordance with the present invention.

Example 4

FIG. 6 is a view showing the compositions of three types of yogurt mixes used in Example 3. First, yogurt mixes of Blends A to C are each prepared by mixing 83.90% by weight of milk (manufactured by Meiji Dairies Corporation), 1.51% by weight of skimmed milk powder (manufactured by Meiji Dairies Corporation), 0.80% by weight of Whey Protein Concentrate (WPC34, manufactured by Domo), and water, based on the total weight of the yogurt mix. The blend ratios of water are different for Blends A to C, as shown in FIG. 6.

The yogurt mixes of Blends A to C are homogenized and disinfected in the same manner as conventionally done, and then the yogurt mixes of Blends A to C are cooled to a temperature of about 40 degrees. After the cooling, the yogurt mixes of Blends A to C are inoculated with 2.00% by weight of lactic acid bacterium starter. As the lactic acid bacterium starter, used is the lactic acid bacterium separated from Meiji Bulgaria Yogurt (manufactured by Meiji Dairies Corporation).

The yogurt mix of Blend B is inoculated with 0.05% by weight of the concentrated cell suspension of Example 1. The yogurt mix of Blend C is inoculated with 0.10% by weight of the concentrated cell suspension of Example 1. The yogurt mix of Blend A is inoculated with no concentrated cell suspension of Example 1.

The yogurt mixes of Blends A to C are each fermented at a temperature of 40 degrees until the lactate concentration becomes about 0.75%, to thereby produce yogurts. Then, the yogurts of Blends A to C are in cold storage at temperatures of 5 degrees and 10 degrees, and the respective lactate concentrations of the yogurts of Blends A to C are measured over usual freshness date of yogurt (about two weeks from the date of manufacture).

Figure 7:
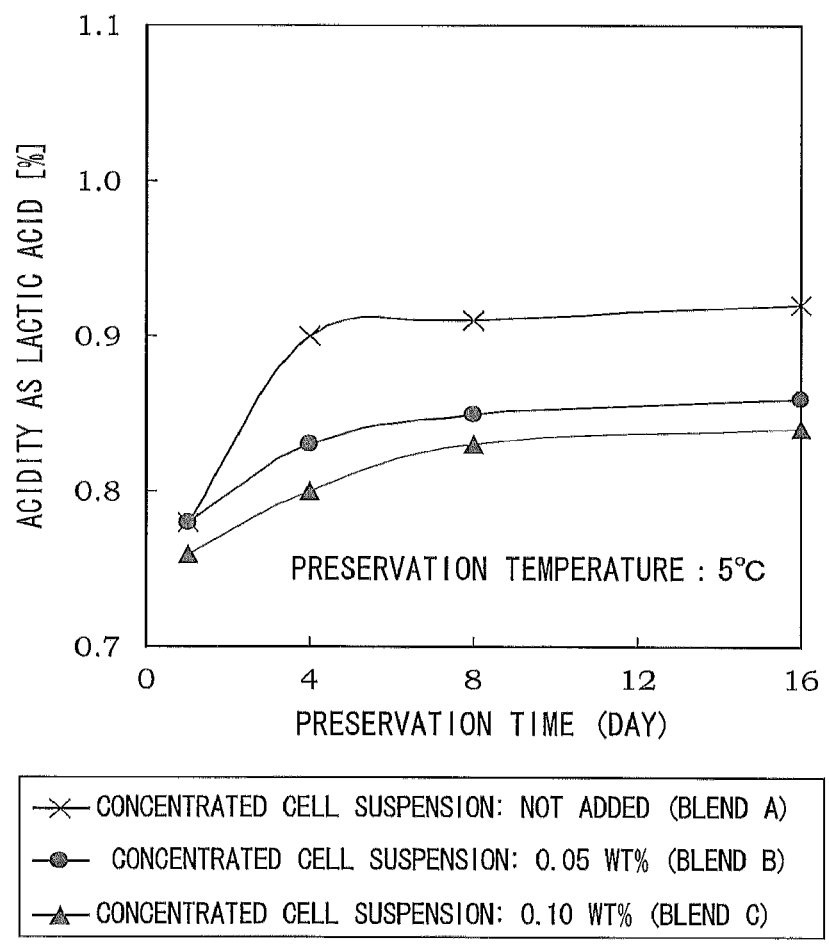
FIG. 7 is a graph showing a change in the acidity over time in a case where yogurts in accordance with Example 4 are preserved at a temperature of 5 degrees.
Figure 8:
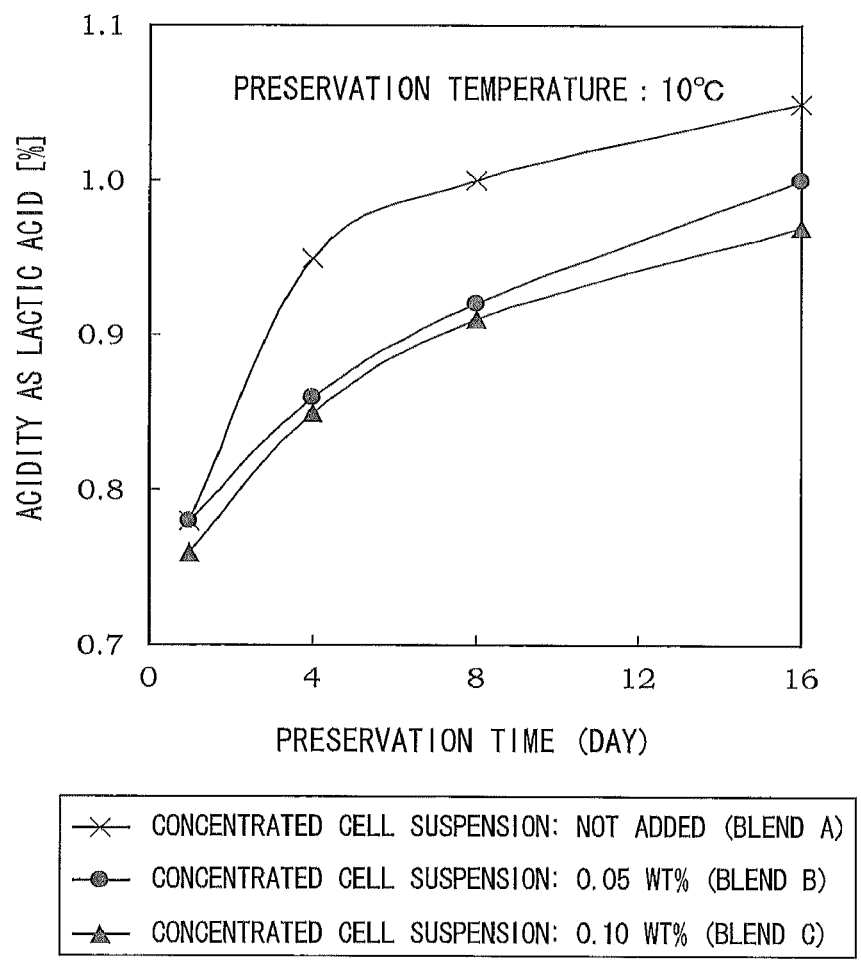
FIG. 8 is a graph showing a change in the acidity over time in a case where yogurts in accordance with Example 4 are preserved at a temperature of 10 degrees.

FIG. 7 is a graph showing a change in the lactate concentration over time in a case where the yogurts of Blends A to C are preserved at a temperature of 5 degrees. FIG. 8 is a graph showing a change in the lactate concentration over time in a case where the yogurts of Blends A to C are preserved at a temperature of 10 degrees.

As shown in FIGS. 7 and 8, regardless of the preservation temperature, the lactate concentrations of the yogurts of Blends B and C are lower than that of the yogurt of Blend A. In other words, it can be clearly seen that the yogurts of Blends B and C, which are inoculated with the concentrated cell suspension of Example 1, are prevented from being fermented in cold storage and can thereby maintain the original flavor and quality thereof.

From the fact that the lactate concentration of the yogurt of Blend C is slightly lower than that of the yogurt of Blend B, it can be seen that an increase in the lactate concentration is more suppressed as the amount of concentrated cell suspension to be inoculated becomes larger. There is, however, a possibility that the original flavor of the yogurt is damaged more as the amount of concentrated cell suspension to be inoculated becomes larger. Since the difference in the lactate concentration between the yogurts of Blends B and C is very small, if it is intended only to suppress an increase in the lactate concentration of the yogurt, the amount of concentrated cell suspension to be inoculated may be in the range from 0.01 to 0.05 WT %.

Further, in the yogurt mixes of Blends B and C, there arises no difference in the effect of suppressing an increase in the lactate concentration of the yogurt between the above case and the case of performing the inoculation with the concentrated cell suspension of Example 1 before the processes for homogenizing and disinfecting the yogurt mix. From this fact, it can be clearly seen that the bacteriocin producer to be inoculated together with the concentrated cell suspension may be dead or alive and whether the bacteriocin producer is dead or alive has no effect on the antibacterial activity of the concentrated cell suspension.

Example 5

Figures 9, 10:
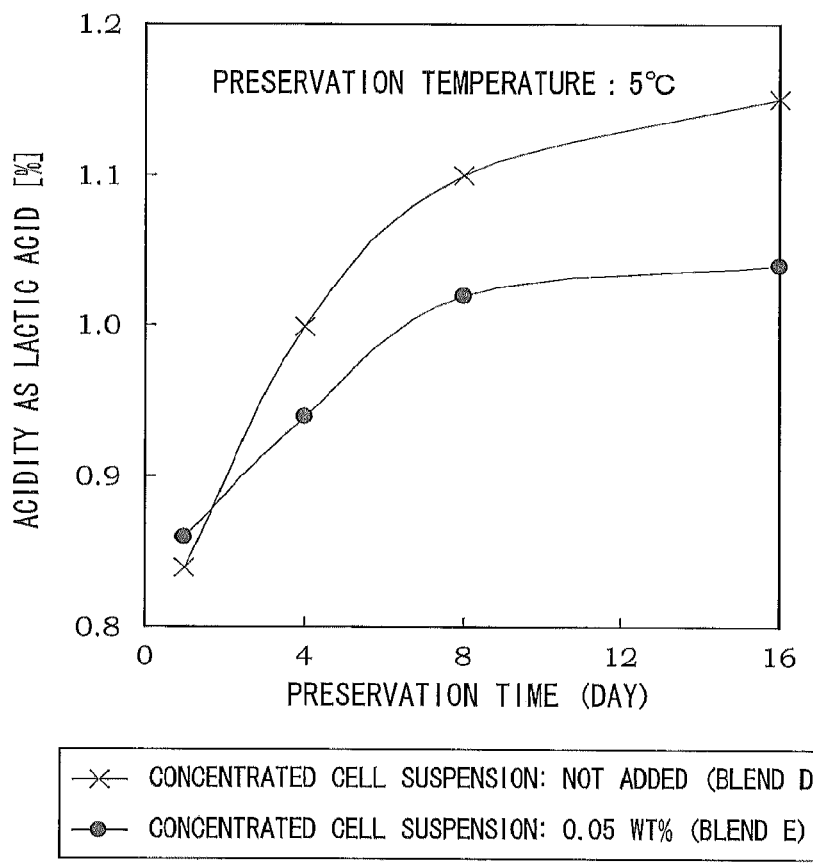
FIG. 9 is a view showing the respective compositions of yogurt mixes used in Example 5.
FIG. 10 is a graph showing a change in the acidity over time in a case where yogurts in accordance with Example 5 are preserved at a temperature of 5 degrees.

FIG. 9 is a view showing the compositions of two types of yogurt mixes used in Example 5. To the yogurt mixes of Example 5, Whey Protein Isolate (WPI) is added, instead of the Whey Protein Concentrate (WPC), and sugar is further added.

First, yogurt mixes of Blends D and E are each prepared by mixing 84.20% by weight of milk (manufactured by Meiji Dairies Corporation), 1.76% by weight of skimmed milk powder (manufactured by Meiji Dairies Corporation), 0.20% by weight of Whey Protein Isolate (WPI, manufactured by New Zealand Milk Products Co., Ltd.), 4.50% by weight of sugar, and water, based on the total weight of the yogurt mix. The blend ratios of water are different for Blends D and E, as shown in FIG. 9.

The yogurt mixes of Blends D and E are homogenized and disinfected in the same manner as conventionally done, and then the yogurt mixes of Blends D and E are cooled to a temperature of about 40 degrees. After the cooling, the yogurt mixes of Blends D and E are inoculated with 3.00% by weight of lactic acid bacterium starter. As the lactic acid bacterium starter, used is the lactic acid bacterium separated from Meiji Tokachi Yogurt (manufactured by Meiji Dairies Corporation). Further, the yogurt mix of Blend E is inoculated with 0.05% by weight of the concentrated cell suspension of Example 1. The yogurt mix of Blend D is inoculated with no concentrated cell suspension of Example 1.

In Example 5, no yogurt mix inoculated with 0.10% by weight of the concentrated cell suspension is used. This is because it is clearly seen in Example 4 that a sufficient effect of suppressing the acidity is achieved even if the amount of concentrated cell suspension to be inoculated is 0.05 WT %.

The yogurt mixes of Blends D and E are each fermented at a temperature of 40 degrees until the lactate concentration becomes about 0.75%, to thereby produce yogurts. Then, the yogurts of Blends D and E are in cold storage at a temperature of 5 degrees, and the respective lactate concentrations of the yogurts of Blends D and E are measured over usual freshness date of yogurt (about two weeks from the date of manufacture).

FIG. 10 is a graph showing a change in the lactate concentrations of the yogurts of Blends D and E over time. As shown in FIG. 10, the lactate concentration of the yogurt of Blend E is lower than that of the yogurt of Blend D. From this fact, it can be clearly seen that it is possible to suppress an increase in the lactate concentration of even yogurt with sugar when the concentrated cell suspension of Example 1 is used for production of the yogurt with sugar.

Further, in the yogurt mix of Blend E, there arises no difference in the effect of suppressing an increase in the lactate concentration of the yogurt between the above case and the case of performing the inoculation with the concentrated cell suspension of Example 1 before the processes for homogenizing and disinfecting the yogurt mix.

In Examples 4 and 5, the amount of concentrated cell suspension of Example 1 to be inoculated as a food preservative is one tenth or less of the amount of food preservative which is conventionally used. In other words, by the method for producing fermented milk discussed in Examples 4 and 5, it is possible to suppress a change in the original flavor of yogurt due to the inoculation with the concentrated cell suspension of Example 1 and maintain the original flavor of yogurt over the freshness date. Further, the same tests as done in Examples 4 and 5 are performed by using the concentrated cell suspension of Example 2. The result is that the yogurt produced by using the concentrated cell suspension of Example 2 can also suppress a change in acidity of the yogurt like in the case of using the concentrated cell suspension of Example 1.

While the invention has been shown and described in detail, the foregoing description is in all aspects illustrative and not restrictive. It is therefore understood that numerous modifications and variations can be devised without departing from the scope of the invention.

The invention claimed is:

1. A method for culturing lactic acid bacteria, comprising the steps of:
   a. adding a proteolytic enzyme to an aqueous whey solution containing whey and water to thereby prepare a culture solution containing whey degraded by the proteolytic enzyme;
   b. inoculating said culture solution with *Lactobacillus gasseri* which is a bacteriocin-producing lactic acid bacteria; and
   c. maintaining said culture solution inoculated with said bacteriocin-producing lactic acid bacteria at a pH of not lower than 5.2 and not higher than 5.8 to provide cultured lactic acid bacteria.

2. The method for culturing lactic acid bacteria according to claim 1, further comprising
   d. separating said bacteriocin-producing lactic acid bacteria from said culture solution in a concentrated form to provide a concentrated cell suspension.

3. The method for culturing lactic acid bacteria according to claim 1, wherein maintaining the pH of said culture solution inoculated with said lactic acid bacteria is accomplished by adding an alkaline solution thereto.

4. The method for culturing lactic acid bacteria according to claim 2, wherein separating to provide said concentrated cell suspension is accomplished by centrifuging said culture solution at a centrifugal acceleration of not lower than 6000 G.

5. A method for producing fermented milk, comprising the steps of:
   a. producing a yogurt mix from raw milk;
   b. providing a concentrated cell suspension containing a bacteriocin producer, which is a bacteriocin-producing lactic acid bacteria belonging to *Lactobacillus gasseri*, in a concentrated form, by culturing including the steps of, in the order recited:
      (i) adding a proteolytic enzyme to an aqueous whey solution containing whey and water to thereby prepare a culture solution containing whey degraded by the proteolytic enzyme;
      (ii) inoculating said culture solution with *Lactobacillus gasseri*, said bacteriocin-producing lactic acid bacteria which is said bacteriocin producer;

(iii) maintaining said culture solution inoculated with said bacteriocin producers at a pH of not lower than 5.2 and not higher than 5.8; and
(iv) separating said bacteriocin producers from said culture solution to provide said concentrated cell suspension;
c. adding said concentrated cell suspension to said yogurt mix in an amount of not less than 0.01% and not more than 0.1% by weight, based on total weight of said yogurt mix; and
d. fermenting said yogurt mix to which said concentrated cell suspension is added to provide said fermented milk.

6. The method for producing fermented milk according to claim 5, wherein the amount of said concentrated cell suspension to be added to said yogurt mix is not less than 0.01 weight % and not more than 0.05 weight %, based on total weight of said yogurt mix.

7. The method for producing fermented milk according to claim 5, wherein maintaining the pH of said culture solution inoculated with said bacteriocin producers is accomplished by adding an alkaline solution thereto.

8. The method for producing fermented milk according to claim 5, wherein separating is accomplished by centrifuging said culture solution at a centrifugal acceleration of not lower than 6000 G.

* * * * *